United States Patent [19]

Grasso

[11] 4,377,531

[45] Mar. 22, 1983

[54] METHOD FOR THE ALKYLATION OF PHENYLACETONITRILES

[75] Inventor: Charles P. Grasso, East Windsor, N.J.

[73] Assignee: American Cyanamid Company, Stamford, Conn.

[21] Appl. No.: 309,301

[22] Filed: Oct. 7, 1981

[51] Int. Cl.$^3$ .................. C07C 121/75; C07C 121/66
[52] U.S. Cl. ........................... 260/465 F; 260/465 R; 260/465 D; 260/465 G; 260/544 D; 562/465; 562/478
[58] Field of Search ............ 260/465 R, 465 F, 465 G

[56] References Cited

U.S. PATENT DOCUMENTS

| | | | |
|---|---|---|---|
| 3,755,412 | 8/1973 | Taranko et al. | 260/465 R |
| 4,012,428 | 3/1977 | Ahno et al. | 260/465 G |
| 4,062,968 | 12/1977 | Fujimoto et al. | 424/304 X |
| 4,307,034 | 12/1981 | Nakayama et al. | 260/465 G |

Primary Examiner—Dolph H. Torrence
Attorney, Agent, or Firm—Thomas J. Monahan

[57] ABSTRACT

A method for the alkylation of certain substituted phenylacetonitriles with alkylhalides in the presence of solid particulated alkali metal hydroxides under essentially anhydrous conditions. Trialkylamine catalysts may optionally be utilized. Compounds obtained by this method, some of which are valuable intermediates in the preparation of pyrethroid pesticides, are described.

10 Claims, No Drawings

METHOD FOR THE ALKYLATION OF PHENYLACETONITRILES

The invention herein described relates to a novel method for the alkylation of various substituted phenylacetonitriles. The method uses alkylhalides in the presence of solid particulated alkali metal hydroxides under essentially anhydrous conditions. Optionally, trialkylamine catalysts may be utilized. Among the various compounds which may be obtained by this method are valuable intermediates useful in the preparation of pyrethroid pesticides. The preparation of pyrethroids from phenylacetonitriles is described in U.S. Pat. No. 4,199,595.

By way of background, several conventional methods for the alkylation of phenylacetonitrile and substituted phenylacetonitriles are known. For example, phenylacetonitrile and substituted phenylacetonitriles can be α-alkylated with various alkyl halides in the presence of a catalyst selected from various quaternary ammonium salts and an appropriate acid acceptor (i.e., aqueous sodium or potassium hydroxide, carbonate, etc.). Other conventional methods effect α-alkylation of phenylacetonitriles by utilizing alkyl halides, anhydrous aprotic solvents, alkali metals, alkali metal amides, or liquid ammonia. However, such conventional methods usually give products which are of unsatisfactory purity and/or yields. In addition, these conventional methods are often cumbersome and require isolation and purification steps before the final products are obtained.

In light of the foregoing summary of the limitations of conventional methods for the alkylation of phenylacetonitriles, an improved method for preparation of these compounds is highly desirable. An object of this invention is to provide a new and useful method for the alkylation of phenylacetonitriles such that quantitatively and qualitatively sufficient yields are obtained so that product isolation and purifications may not be necessary. This object is manifest in the following description and particularly delineated in the appended claims.

A method for the preparation of compounds having the following structural formula has been discovered:

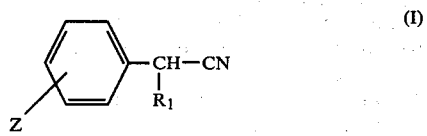

wherein Z is $C_1$-$C_4$ alkyl, $C_1$-$C_4$ alkoxy or halogen and $R_1$ is $C_1$-$C_4$ alkyl. The method comprises reacting a compound of the following structural formula:

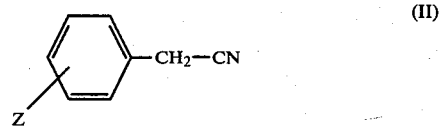

with an alkyl halide of formula $R_1$-X in the presence of an anhydrous alkali metal hydroxide, wherein Z is $C_1$-$C_4$ alkyl, $C_1$-$C_4$ alkoxy or halogen; $R_1$ is $C_1$-$C_4$ alkyl; and X is Cl, Br, or I. A preferred group of formula-I compounds are those where Z is in the para position and is methyl, methoxy, or chloro and $R_1$ is isopropyl. The most preferred formula-I compound is 2-(4-methoxyphenyl)-3-methylbutyronitrile which is represented by the following structural formula:

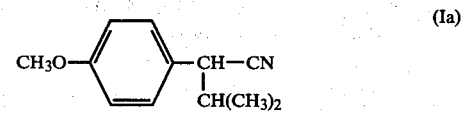

Formula-I compounds are especially the compound represented by formula-(Ia) are valuable intermediates for the preparation of broad-spectrum pyrethroid insecticides.

The method of the invention is graphically illustrated by the following equation:

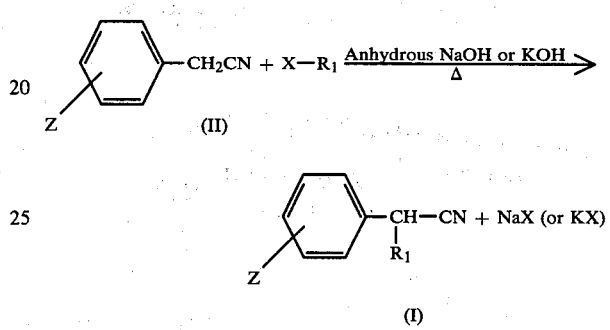

wherein Z is $C_1$-$C_4$ alkyl, $C_1$-$C_4$ alkoxy, or halogen; $R_1$ is $C_1$-$C_4$ alkyl; and X is Cl, Br or I. One mole of a substituted phenylacetronitrile of formula-(II) is added at a temperature range of about 20° C. to 100° C. (preferably 50° C. to 60° C.) over a 30 to 60 minute period to a stirred mixture comprising: (1) one to four moles (preferably two to three moles) of an alkylating agent of formula $R_1$-X; (2) one to five moles (preferably three to four moles) of solid particulated potassium or sodium hydroxide (preferably sodium hydroxide pels); and (3) 0 to 12% by weight or 0 to 12 mol percent of a $C_1$-$C_4$ trialkylamine (preferably triethylamine). Larger amounts of trialkylamine may be incorporated into the above reaction mixture, but such use does not significantly improve either product yield or purity. The reaction mixture is then stirred and heated to a temperature between about 20° C. and 100° C. (preferably 68°-75° C.) or at reflux until the reaction is essentially complete.

The compound 2-(4-methoxyphenyl)-3-methylbutyronitrile (i.e., formula-Ia compound) can be prepared by the above-described method. One mole of 4-methoxyphenylacetonitrile is added over a 30-minute period at a temperature range of about 50° to 60° C. to a stirred mixture of 2 moles of isopropyl bromide, 4 moles of sodium hydroxide pels, and 11 mol percent of triethylamine. The reaction mixture is then stirred and heated at reflux (i.e., 68° to 75° C.) for 6 hours. Following completion of the reaction, the mixture is diluted with water and the organic phase is separated. The organic phase containing the product is then optionally washed with water and used in this form, or the product may be isolated from the organic phase if it is so desired. The product, 2-(4-methoxyphenyl)-3-methylbutyronitrile, is obtained in high yield (i.e., approximately 96%). A similar method of preparation with the exception that the triethylamine reactant is omitted gives a comparable product yield (i.e., 99%).

Formula-I compounds are valuable intermediates for the preparation of pyrethroid pesticides. Such a preparation is illustrated and discussed below using 2-(4-methoxyphenyl)-3-methylbutyronitrile (i.e., formula-Ia compound) as starting material:

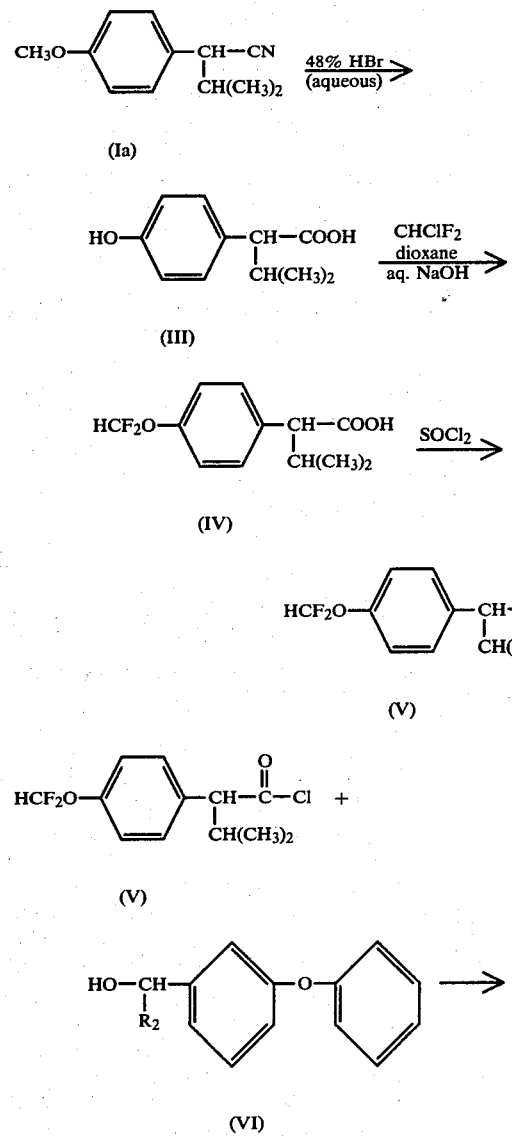

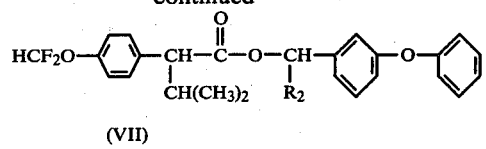

(VII)

wherein $R_2$ is hydrogen or CN. As can be seen from the preceding graphic representation, 2-(4-methoxyphenyl)-3-methylbutyronitrile (Ia) is hydrolyzed with aqueous 48% hydrobromic acid to produce 2-(4-hydroxyphenyl)-3-methylbutyric acid (III). Treatment of this acid (III) with chlorodifluoromethane in the presence of dioxane and aqueous sodium hydroxide yields 2-(4-difluoromethoxyphenyl)-3-methylbutyric acid (IV). This acid (IV) is then converted to the corresponding acid chloride (V) which in turn is reacted with an appropriate m-phenoxybenzyl alcohol of (VI) in the presence of an acid acceptor to yield the desired pyrethroid (VII) insecticide.

The invention herein described is further illustrated by the following examples which are not to be taken as limitative thereof.

EXAMPLE 1

General Method of Preparation Of 2-(4-methoxyphenyl)-3-methylbutyronitrile

A mixture comprising: isopropyl bromide, sodium hydroxide pels, and optionally the catalyst triethylamine (i.e., approximately 0.5 to 12 mol or weight percent) is stirred and heated to 50°–60° C. Over approximately a 30-minute period 4-methoxyphenylacetonitrile is added to the reaction mixture. Following this addition, the mixture is stirred and heated at reflux for several hours. After cooling, water is added to the reaction mixture which is then stirred briefly. The organic phase containing the product is then separated. This solution can be used in subsequent reaction steps or the product can be isolated by removal of the solvents.

Using the above-described general method, several individual preparations are made. The results of these experiments are presented in Tables Ia to Ic. These data clearly indicate that equally good results are obtained in the preparation of 2-(4-methoxyphenyl)-3-methylbutyronitrile with or without the use of the catalyst triethylamine. These data also indicate that product yield increases with increasing amounts of anhydrous sodium hydroxide, thus suggesting the importance of carrying out the reaction under anhydrous conditions. In the above-described method of preparation anhydrous potassium hydroxide can be substituted for anhydrous sodium hydroxide (c.f., Table Ic, No. 12). However, substitution of aqueous sodium hydroxide for anhydrous sodium hydroxide produces a lower yield of product (c.f., Table Ic, No. 11).

TABLE Ia

Preparation of 2-(4-methoxyphenyl)-3-methylbutyronitrile

| No | NaOH pels mol + | $(CH_3)_2CH$—Br mol + | $(C_2H_5)_3N$ mol (m) or wt(w) % | Reaction temperature in °C. | time in h | G.C. Analysis % product | % * | Reaction scale in mol | product in g | Assay of Product % purity | % yield |
|---|---|---|---|---|---|---|---|---|---|---|---|
| 1 | 4 | 2 | (m) 11 | 68–75 | 6 | 95.6 | | | | — | — |
| 2 | 4 | 2 | (m) 11 | 68–75 | 6 | 95.0 | | | | — | — |
| 3 | 4 | 2 | (m) 11 | 68–75 | 6 | 93.6 | | | | — | — |
| 4 | 4 | 2 | (m) 1 | 68–75 | 6 | 95.6 | | | | — | — |
| 5 | 4 | 2 | (m) 0.5 | 68–75 | 6 | 95.5 | | | | — | — |
| 6 | 4 | 2 | — | 68–74 | 4 | — | | | | 96.7 | |

TABLE Ia-continued

Preparation of 2-(4-methoxyphenyl)-3-methylbutyronitrile

| No | NaOH pels mol + | $(CH_3)_2CH-Br$ mol + | $(C_2H_5)_3N$ mol (m) or wt(w) % | Reaction temperature in °C. | time in h | G.C. Analysis % product | % * | Reaction scale in mol | product in g | Assay of Product % purity | % yield |
|---|---|---|---|---|---|---|---|---|---|---|---|
| 7 | 4 | 2 | — | 68-74 | 4 | 96.27 | 0.54 | 2.0 | 367.88 | 96.9 | 99.1 |
| 8 | 4 | 2 | — | 68-74 | 3 | 96.17 | 0.53 | | | | |
| 9 | 4 | 2 | — | 68-74 | 4 | 92.0 | 0.1 | | | | |
| 10 | 4 | 2 | — | 68-74 | 3 | 95.48 | 1.4 | | | | |

* = unreacted 4-methoxyphenylacetonitrile
+ = per mol of 4-methoxyphenylacetonitrile

TABLE Ib

Preparation of 2-(4-methoxyphenyl)-3-methylbutyronitrile

| No | NaOH Pels mol + | $(CH_3)_2CH-Br$ mol + | $(C_2H_5)_3N$ mol (m) or wt(w) % | Reaction temperature in °C. | time in h | G.C. Analysis % product | % * | Reaction scale in mol | product in g | Assay of Product % purity | % yield |
|---|---|---|---|---|---|---|---|---|---|---|---|
| 1 | 4 | 3 | (m) 10 | 70 | 8 | 97.78 | 0.67 | 0.2 | 36.11 | 95.3 | 95.8 |
| 2 | 4 | 3 | (w) 10 | 70 | 7 | 96.24 | 1.04 | 2.0 | 358.05 | 95.4 | 94.99 |
| 3 | 4 | 3 | (w) 10 | 70 | 7 | 96.63 | 1.09 | 2.0 | 371.0 | 93.8 | 96.5 |
| 4 | 4 | 3 | (w) 12 | 70 | 3 | 96.45 | 0.80 | 2.0 | 379.5 | 90.3 | 95.45 |
| 5 | 4 | 3 | (m) 11 | 68-74 | 6 | 94.97 | 1.49 | 2.0 | 345.15 | 93.2 | 96.99 |
| 6 | 4 | 3 | (m) 11 | 68-74 | 6 | 95.2 | 0.90 | 4.0 | 711 | 93.0 | 92.0 |
| 7 | 4 | 3 | (m) 11 | 68-74 | 6 | 94.67 | 2.38 | 4.0 | 737 | 95.6 | 98.0 |
| 8 | 4 | 3 | (m) 11 | 68-74 | 6 | 95.47 | 0.38 | 4.0 | 759 | 94.4 | 99.0 |
| 9 | 4 | 3 | (m) 11 | 68-74 | 6 | 95.45 | 0.38 | | | — | — |

* = unreacted 4-methoxyphenylacetonitrile
+ = per mol of 4-methoxyphenylacetonitrile

TABLE Ic

Preparation of 2-(4-methoxyphenyl)-3-methylbutyronitrile

| No | NaOH pels mol + | $(CH_3)_2CH-Br$ mol + | $(C_2H_5)_3N$ mol (m) or wt(w) % | Reaction temperature in °C. | time in h | G.C. Analysis % product | % * | Reaction scale in mol | product in g | Assay of Product % purity | % yield |
|---|---|---|---|---|---|---|---|---|---|---|---|
| 1 | 1.1 | 2.0 | — | 68-74 | 6 | 63.6 | 33.96 | | | | |
| 2 | 2.2 | 1.15 | (w) 10 | 70-75 | 5 | 81.0 | 18 | | | | |
| 3 | 2.2 | 1.15 | (w) 10 | 70-75 | 24 | 92.7 | 4.7 | | | | |
| 4 | 2.2 | 1.15 | (w) 10 | 65-70 | 24 | 90.9 | 6.2 | | | | |
| 5 | 2.2 | 1.25 | (w) 10 | 70-75 | 18 | 92.1 | 5.6 | | | | |
| 6 | 2.2 | 1.25 | (w) 10 | 90-100 | 4 | 88.12 | 8.78 | | | | |
| 7 | 2.2 | 3.0 | (w) 11 | 70 | 10 | 92.0 | 6.5 | 0.2 | 34.85 | 92.0 | 89.3 |
| 8 | 2.2 | 3.0 | (w) 11 | 70 | 12 | 95.8 | 2.5 | 0.2 | 35.73 | 93.2 | 93.0 |
| 9 | 3.0 | 1.25 | (w) 11 | 68-74 | 6 | 95.0 | 1.5 | | | | |
| 10 | 3.0 | 1.25 | (w) 11 | 68-74 | 5 | 92.76 | 4.09 | | | | |
| 11 | 5.72** | 1.25 | BTEAC 5 | 55-60 | 24 | 85.5 | 10.7 | 0.2 | 34.34 | 84.4 | 77.0 |
| 12 | KOH 2.2 | 1.25 | $(C_2H_5)_3N$ 12 | 70-75 | 24 | 80.4 | 10.91 | | | — | — |

* = untreated 4-methoxyphenylacetonitrile
** = 50% aqueous sodium hydroxide
+ = per mol of 4-methoxyphenylacetonitrile
BTEAC = Benzyl triethylammonium chloride

EXAMPLE 2

Preparation of 2-(4-methoxyphenyl)-3-methylbutyronitrile

To a stirred suspension of sodium hydroxide pels (320.0 g; 8.0 mol) in isopropyl bromide (492.0 g; 4.0 mol) is added 4-methoxyphenylacetonitrile (294.3 g; 2.0 mol) over a 30-minute period at a temperature of 50°-55° C. Following this addition the reaction mixture is stirred at reflux (68°-74° C.) for 4 hours. It is then cooled to 50° C. and water (498 ml) is added. The mixture is subsequently stirred for 15 minutes with cooling. The aqueous and organic phases are then separated and the excess isopropyl bromide is removed from the organic phase by distillation. The resulting product (367.88 g of 2-(4-methoxyphenyl)-3-methylbutyronitrile) is 96.9% pure and corresponds to a real yield of 99.1%. The results of this experiment are included in Table Ia under No. 7.

EXAMPLE 3

Preparation of 2-(4-methoxyphenyl)-3-methylbutyronitrile

To a stirred mixture of isopropyl bromide (246.0 g; 2.0 mol), triethylamine (160.0 g; 4.0 mol), and solid sodium hydroxide pels (160.0 g; 4.0 mol) is added 4-methoxyphenylacetonitrile (147.18 g, 95% pure=139.85 g; 0.95 mol) over a 30-minute period at 60° C. Following this addition the reaction mixture is stirred at 68°-74° C. for 6 hours. The reaction mixture is then cooled to 45° C. and water (205 ml) is added. The mixture is subsequently stirred for 15 minutes with cooling. The organic and aqueous phases are then separated and the excess isopropyl bromide and triethylamine is distilled from the organic phase. This method gives 189.7 g of product which is 92.6% pure. This corresponds to an effective yield of 98.7%.

EXAMPLE 4

Preparation of
2-(4-chlorophenyl)-3-methylbutyronitrile

The compound 2-(4-chlorophenyl)-3-methylbutyronitrile can be prepared by the following two methods:

(1) To a stirred mixture of isopropyl bromide, sodium hydroxide pels, and triethylamine is added 4-chlorophenylacetonitrile at reflux temperature until gas chromatographic analysis of a sample removed from the reaction mixture indicates no further change.

(2) To a stirred mixture of isopropyl bromide, sodium hydroxide pels, and triethylamine is added 4-chlorophenylacetonitrile over a 20-minute period at 55° C. Following this addition the mixture is stirred at reflux until gas chromatographic analysis of a sample removed from the reaction mixture indicates no further change.

Several preparations are made using one or the other of the above methods. Results of these experiments are presented in Table 2. The reactants used are expressed in terms of the number of moles used per mole of 4-chlorophenylacetonitrile. These data indicate that the product yield is significantly reduced in the absence of the triethylamine catalyst.

TABLE 2

| | | Preparation of 2-(4-chlorophenyl)-3-methylbutyronitrile | | | | | |
|---|---|---|---|---|---|---|---|
| | Scale | NaOH | | | Reaction | | G.C. Analysis |
| No | of Reaction | pels mol | $(CH_3)_2CHBr$ mol | $(C_2H_5)_3N$ mol % | temperature (°C.) | time (hrs) | % product | * % |
| 1 | .2 mol | 4 | 3 | 11 | 68–70 | 6 | 97.94 | 1.62 |
| 2 | .2 mol | 4 | 2 | — | 68–74 | 6 | 52.0 | 47.73 |
| 3 | .1 mol | 4 | 2 | 10 | 75 | 1.5 | 98.18 | 0.42 |

* = unreacted 4-chlorophenylacetonitrile

EXAMPLE 5

Preparation of 2-(4-hydroxyphenyl)-3-methylbutyric acid

A mixture of 2-(4-methoxyphenyl)-3-methylbutyronitrile (40.0 g; 0.21 mol) and hydrobromic acid (48%; 200 ml) is refluxed at 126°–128° C. for 14 hours. The reaction mixture is diluted with ice and water and extracted several times with ether. The ether extracts are combined, washed with water, and evaporated to obtain a solid residue. The solid product is boiled with chloroform (200 ml), cooled, filtered and dried. This procedure yields 23.8 g of product having a melting point of 172°–174° C.; ir (Nujol) 3250–2900 (broad, OH), 1690 cm$^{-1}$ (C=O).

EXAMPLE 6

Preparation of 2-(4-difluoromethoxyphenyl)-3-methylbutyric acid

To a stirred mixture of 2-(4-hydroxyphenyl)-3-methylbutyric acid (10.0 g; 0.0515 mol), dioxane (65 ml), sodium hydroxide (19.08 g, 18.56 g real; 0.464 mol), and water (30 ml) is bubbled chlorodifluoromethane (46 g; 0.532 mol) at 80° C. over a four-hour period. The reaction mixture is then poured into 250 ml of ice water, washed with ether, acidified with concentrated hydrochloric acid to pH 3, and extracted with 200 ml of ether. The ether extract is washed with 100 ml of water, dried with sodium sulfate, filtered, and evaporated to a white paste. A mixture of hexane and methylene chloride is added. The resulting mixture is filtered to remove the solid which is the starting material. The filtrate is evaporated to give 5.41 g of product as a clear brown oil. The product is at least 85% pure as calculated by NMR. NMR (CDCl$_3$-d$_5$ pyridine): $\delta$6.57 (t, J=74.3 Hz, 1H); $\delta$3.63 (s, imp.); $\delta$3.25 (d, J=10 Hz, 1H); $\delta$2.37 (m, 1H); $\delta$1.19 (d, J=6.5 Hz, 3H); $\delta$0.78 (d, J=6.5 Hz, 3H); $\delta$13.82 (s, 1H).

EXAMPLE 7

Preparation of 2-(4-difluoromethoxyphenyl)-3-methylbutyryl chloride

A solution of 2-(4-difluoromethoxyphenyl)-3-methylbutyric acid (4.39 g) and thionyl chloride (3.7 ml) in benzene (20 ml) is refluxed for 4 hours. Evaporation of the solvent and excess thionyl chloride gives the acid chloride which is used for esterification. IR band: 1800 cm$^{-1}$.

EXAMPLE 8

Preparation of α-Cyano-m-phenoxybenzyl α-Isopropyl-4-difluoromethoxyphenylacetate A solution of 2-(4-difluoromethoxyphenyl)-3-methylbutyryl chloride (4.82 g) in methylene chloride (10 ml) is added to a methylene chloride solution (10 ml) of α-cyano-m-phenoxybenzyl alcohol (4.05 g) and pyridine (1.5 ml). The mixture is stirred for approximately 60 hours and filtered. The filtrate and the washings are evaporated and the residual oil (6.29 g) is purified on a silica column using 1:1 methylenechloride-hexane as an eluant. The solvent is evaporated and the residue treated with sodium borohydride. The resulting crude material is purified on a silica gel column to yield 2.01 g of product.

NMR (CDCl$_3$): $\delta$0.88 (four doublets, J=6 Hz, 6H, CH$_3$); $\delta$2.30 [m, 1H, —CH—CH(CH$_3$)$_2$]; $\delta$3.24 [d, J=10.1 Hz, 1H, —C$\underline{H}$—CH(C$\underline{H}_3$)$_2$]; $\delta$6.33 (two singlets, 1H, —C$\underline{H}$CN); $\delta$6.45 (t, J=74 Hz, 1H, C$\underline{H}$F$_2$O—); $\delta$7.16 (m, 13H, ArH).

Analysis calculated for C$_{26}$H$_{23}$F$_2$NO$_4$: C, 69.17%; H, 5.13%; F, 8.42%, N, 3.10%. Found: C, 69.41%; H, 5.20%; F, 10.25%; N, 3.70%.

EXAMPLE 9

Resolution of α-2-(4-difluoromethoxyphenyl)-3-methylbutyric acid

A warm solution (60° C.) of (-)-2-phenethylamine (4.96 g) in aqueous ethanol (60% ethanol, 20 ml) is added to a stirred warm solution (60° C.) of racemic α-2-(4-difluoromethoxyphenyl)-3-methylbutyric acid (20 g) in aqueous ethanol (60% ethanol, 50 ml). As the solution is allowed to cool slowly to room temperature, the salt precipitates out as a white crystalline solid. The mixture is allowed to stand overnight. The precipitated solids are collected by filtration, washed with aqueous ethanol (10 ml) and dried (9.5 g). The salt thus obtained has a melting point from 184° to 188° C. The resolved acid obtained from the above salt has a rotation of: $[\alpha]_D^{R.T} = +37.1°$ (CHCl$_3$, C=1.439 g/100 ml). Two additional crystallizations of the above salt from aqueous ethanol (60% ethanol) give white needles with a melting point from 185° to 187° C. from which the resolved acid is obtained. This product has a rotation of: $[\alpha]_D^{R.T} = +40.4°$ (CHCl$_3$, C=1.353 g/100 ml).

EXAMPLE 10

Preparation of (+) 2-(4-difluoromethoxyphenyl)-3-methylbutyryl chloride

The compound (+) 2-(4-difluoromethoxyphenyl)-3-methyl-butyryl chloride can be prepared by treating a solution of (+)-2-(4-difluoromethoxyphenyl)-5-methylbutyric acid with thionyl chloride in benzene as described in Example 7 above.

EXAMPLE 11

Preparation of (+)-α-Cyano-m-phenoxybenzyl (+)-α-Isopropyl-4-difluoromethoxyphenylacetate The compound (+)-α-cyano-m-phenoxybenzyl (+)-α-isopropyl-4-difluoromethoxyphenylacetate can be prepared by treating a solution of (+)-2-(4-difluoromethoxyphenyl)-3-methylbutyryl chloride in methylene chloride with α-cyano-m-phenoxybenzyl alcohol in methylene chloride and pyridine as described in Example 8 above.

The compound (+)-α-cyano-m-phenoxybenzyl (+)-α-isopropyl-4-difluoromethoxyphenylacetate is a colorless viscous oil. N$_D^{23}$=1.5432; NMR (CDCl$_3$) δ6.8 to 7.5 (m, 13H, ArH); δ6.73 (t, J=74 Hz, 1H, OCHF$_2$); δ6.30 and 6.23 (2S, 1H, CH—CN); δ3.27 [d, J=10 Hz, 1H, C$\underline{H}$—CH(CH$_3$)$_2$].

What is claimed is:

1. A method for the preparation of compounds of structural formula:

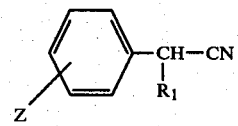

wherein Z is C$_1$-C$_4$ alkyl, C$_1$-C$_3$ alkoxy or halogen; R$_1$ is C$_1$-C$_4$ alkyl; comprising reacting one mole of a compound of the structural formula:

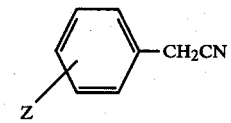

with from one to four moles of a compound of formula R$_1$-X, wherein Z and R$_1$ are as defined above and X is halogen, in the presence of from one to five moles of solid particulated potassium or sodium hydroxide at a temperature from 20° to 100° C. or at the reflux temperature of the mixture, until the reaction is essentially complete.

2. A method according to claim 1 wherein the reaction mixture contains from 0.5 to 12 mol or weight percent of a C$_1$-C$_4$ trialkylamine catalyst.

3. A method according to claim 2 wherein the compound is the para isomer, and Z is methyl, methoxy, chloro or bromo; R$_1$ is isopropyl.

4. A method according to claim 3 wherein the compound is 2-(4-chlorophenyl)-3-methylbutyronitrile.

5. A method according to claim 3 wherein the compound is 2-(4-chlorophenyl)-3-methylbutyronitrile.

6. A method according to claim 4 wherein one mole of 4-methoxyphenylacetonitrile is reacted with from two to three moles of isopropyl bromide in the presence of four moles of solid, particulated, sodium hydroxide at a temperature from 68° to 75° C. for four to six hours.

7. A method according to claim 6 wherein the reaction mixture contains about 10 to 12 mol or weight percent of triethylamine catalyst per mole of 4-methoxyphenylacetonitrile.

8. A method according to claim 6 wherein two moles of isopropyl bromide are used.

9. A method according to claim 6 wherein three moles of isopropyl bromide are used.

10. A method according to claim 5 wherein one mole of 4-chlorophenylacetonitrile is reacted with two to three mole of isopropyl bromide in the presence of four moles of solid, particulated, sodium hydroxide and 9 to 12 mol or weight percent of triethylamine at a temperature from 68° to 75° C. for 1.5 to 6 hours.

* * * * *